United States Patent [19]

Bailey

[11] 4,207,418

[45] Jun. 10, 1980

[54] 1,2-ETHANEDIAMINE SALTS OF NALIDIXIC ACID

[75] Inventor: Denis M. Bailey, East Greenbush, N.Y.

[73] Assignee: Sterling Drug Inc., New York, N.Y.

[21] Appl. No.: 948,956

[22] Filed: Oct. 5, 1978

[51] Int. Cl.² .................................. C07D 471/04
[52] U.S. Cl. .................... 546/123; 546/122; 424/256
[58] Field of Search ..................... 546/122, 123

Primary Examiner—Alan L. Rotman
Attorney, Agent, or Firm—R. K. Bair; B. W. Wyatt

[57] ABSTRACT

1:1 and 1:2 molar salts of 1,2-ethanediamine and nalidixic acid are prepared by reacting 1,2-ethanediamine with one or two molar equivalents of nalidixic acid. Also shown are aqueous solutions of the 1:1 equimolar salt and their preparation from the corresponding 1:2 molar salt.

3 Claims, No Drawings

1,2-ETHANEDIAMINE SALTS OF NALIDIXIC ACID

BACKGROUND OF THE INVENTION (a) Field of the Invention

This invention related to diamine salts of 1-alkyl-1,4-dihydro-4-oxo-1,8-naphthyridine-3-carboxylic acid, to solutions containing said salts and to a process for their preparation.

(b) Description of the Prior Art

Sterling Drug Inc. G. Y. Lesher and M. D. Gruett U.S. Pat. No. 3,590,036, issued June 29, 1971, shows, inter alia, 1-alkyl-1,4-dihydro-4-oxo-7-alkyl-1,8-naphthyridine-3-carboxylic acids and salts thereof as antibacterial agents, a preferred embodiment being 1-ethyl-1,4-dihydro-7-methyl-4-oxo-1,8-naphthyridine-3-carboxylic acid, a commercially available drug generically known as nalidixic acid. Among the salts shown are the 3-carboxylic cationic salts with preferred salts being:

"These comprise the alkali metal salts, e.g., the sodium or potassium salts; the lower-alkaline earth metal salts, e.g., magnesium or calcium salts; and, the ammonium or organic amine salts, e.g., diethanolamine or N-methylglucamine salts."

Among the organic cationic salts specifically disclosed for nalidixic acid are its N-methylglucamine salt (Example 108) and its 4-sulfamoylbenzylammonium salts (Example 349).

An abstract [C.A. 76, 126372k (1972)] of Soc. d'Etudes de Produits Chimiques French Demande 2,070,673, filed Oct. 22, 1971, shows virustatic alkylenediamine salts which were prepared by reaction of ethylenediamine (I) with the appropriate acid in refluxing methanol or by reacting the calcium salt of the appropriate acid with ethylenediamine dihydrochloride in water. Shown are the following salts of ethylenediamine: "camphorate, α-furoate, 5-nitro-α-furoate, 5-bromo-α-furoate, cyclohexamate, 2-oxobornane-3-sulfonate, pyridinesulfonate, benzoate, 5-methyl-8-hydroxyquinoline-7-sulfonate, nicotinate, β-dodecylsulfate and thiophenesulfonate". These compounds are also shown in the corresponding British Pat. Nos. 1,176,077 and 1,268,557, published respectively on Jan. 1, 1970 and Mar. 29, 1972.

Belgian Pat. No. 827,639, published July 31, 1975 shows, as agents for treating respiratory tract infections, and as having bronchodilator, respiratory analeptic and mucolidic activities, salts of ethylenediamine with theophylline alkanoic acids and S-containing amino acids. Preferably used were 7-theophylline acetic acid or its 8-chloro or bromo derivative and the S-containing amino acids used were cysteine, methionine, N-acetyl-methionine, N-acetyl-thiazolidine carboxylic acid, N-acetyl-cysteine or S-carboxymethyl cysteine. The corresponding U.S. Pat. No. 4,071,517, issued Jan. 31, 1978.

SUMMARY OF THE INVENTION

In a composition aspect, the invention relates to the 1:1 and 1:2 molar salts of ethylenediamine (same as 1,2-ethanediamine) and 1-ethyl-1,4-dihydro-4-methyl-4-oxo-1,8-naphthyridine-3-carboxylic acid, the parent acid known generically as nalidixic acid, a commercial antibacterial agent. Said salts are useful as antibacterial agents and are particularly useful in the preparation of aqueous solutions of the 1:1 equimolar salt of 1,2-ethanediamine and nalidixic acid.

In a process aspect the invention relates to a process of reacting 1,2-ethanediamine with one or two molar equivalents of 1-ethyl-1,4-dihydro-7-methyl-4-oxo-1,8-naphthyridine-3-carboxylic acid to produce the 1:1 or 1:2 molar salt of 1,2-ethanediamine and nalidixic acid.

In another process aspect, the invention relates to the conversion of the 1:2 molar salt of 1,2-ethanediamine and nalidixic acid to produce a mixture of an aqueous solution containing the 1:1 equimolar salt of 1,2-ethanediamine and precipitated nalidixic acid, and converting said mixture to said solution by adding 1,2-ethanediamine. Alternatively, this conversion is accomplished directly by treating the 1:2 molar salt of 1,2-ethanediamine and nalidixic acid with water containing sufficient 1,2-ethanediamine to generate the corresponding 1:1 equimolar salt in solution.

In another composition aspect the invention relates to an aqueous solution containing the 1:1 equimolar salt of 1,2-ethanediamine and nalidixic acid.

DETAILED DESCRIPTION INCLUSIVE OF PREFERRED EMBODIMENTS

In a composition aspect, the invention resides in the 1:1 and 1:2 molar salts of 1,2-ethanediamine and 1-ethyl-1,4-dihydro-7-methyl-4-oxo-1,8-naphthyridine-3-carboxylic acid, that is, nalidixic acid. These salts, as shown below, are useful preferably in the preparation of aqueous solutions of the 1:1 equimolar salt of 1,2-ethanediamine and nalidixic acid.

In a process aspect, the invention resides in the process of reacting 1,2-ethanediamine with one or two molar equivalents of 1-ethyl-1,4-dihydro-7-methyl-4-oxo-1,8-naphthyridine-3-carboxylic acid to produce the 1:1 or 1:2 molar salt of 1,2-ethanediamine and nalidixic acid.

In another process aspect, the invention resides in the process of reacting the 1:2 molar salt of 1,2-ethanediamine with water to form a mixture of an aqueous solution of the 1:1 equimolar salt of 1,2-ethanediamine and nalidixic acid and precipitated nalidixic acid and then treating the mixture with sufficient 1,2-ethanediamine to dissolve the nalidixic acid and result in an aqueous solution of its 1:1 equimolar salt with 1,2-ethanediamine. Alternatively, this aspect of the invention is accomplished directly by treating the 1:2 molar salt of 1,2-ethanediamine and nalidixic acid with water containing sufficient 1,2-ethanediamine to generate the corresponding 1:1 equimolar salt in solution.

In another composition aspect, the invention resides in an aqueous solution containing the 1:1 equimolar salt of 1,2-ethanediamine and nalidixic acid. Preferred solutions have a pH value within the range of about 8.0 and 10.5, and particularly preferred embodiments have a pH of about 8.3 and 9.0. The solutions as prepared (containing a nalidixic acid equivalent from about 25 to 100 mg./ml.) can be used as such or they can be diluted with saline solution to prepare injectable formulations having a pH range of about 8.0 to 9.0.

The molecular structure of the salt composition aspect of the invention was assigned on the basis of evidence provided by infra red spectra, and, by the correspondence of calculated and found values for the elementary analyses.

The manner of making and using the instant invention will now be generally described so as to enable a person skilled in the art of pharmaceutical chemistry to make and use the same, as follows:

The process of reacting ethylenediamine with two molar equivalents of 1-ethyl-1,4-dihydro-7-methyl-4-oxo-1,8-naphthyridine-3-carboxylic acid to produce the 1:2 molar salt of ethanediamine and 1-ethyl-1,4-dihydro-7-methyl-4-oxo-1,8-naphthyridine-3-carboxylic acid is carried out preferably by adding nalidixic acid portionwise to an excess of ethylenediamine, preferably with stirring at about room temperature (about 20°–25° C.) to about 100° C. and under an inert atmosphere. Alternatively, one mole of ethylenediamine per two moles of nalidixic acid are thoroughly mixed, either ingredient added to the other, under an inert atmosphere in sufficient water to produce a solution, warming if necessary.

The 1:2 molar salt of ethylenediamine and nalidixic acid in solid form is obtained by carrying out the above-described preparation using a minimum amount of water and heating one mole of ethylenediamine per two moles of nalidixic acid at about 60° to 100° C., preferably about 70° to 80° C., under an inert atmosphere, e.g., nitrogen, and then cooling the solution whereupon the precipitated 1:2 molar salt of 1,2-ethanediamine and nalidixic acid is collected and dried, preferably under an inert atmosphere.

The aqueous solution containing the 1:1 equimolar salt of 1,2-ethanediamine and nalidixic acid is prepared directly and preferably by reacting equimolar quantities of 1,2-ethanediamine and nalidixic acid in water at ambient temperature (about 20°–25° C.) to about 100° C. Alternatively, this solution of 1:1 equimolar salt can be prepared from the 1:2 molar salt of 1,2-ethanediamine and nalidixic acid by treating it with water to produce a mixture containing an aqueous solution of the 1:1 equimolar salt of 1,2-ethanediamine and nalidixic acid and precipitated nalidixic acid, and then reacting the precipitated nalidixic acid with sufficient 1,2-ethanediamine to bring the acid into solution as its 1:1 equimolar salt with the diamine. Optionally, the solution of the 1:1 salt is prepared by adding the 1:2 salt to water containing sufficient 1,2-ethanediamine to generate the corresponding 1:1 salt in solution. This solution can be obtained directly without actually isolating said 1:1 salt, and where desired, the resulting solution can be further diluted with saline solution, that is, an aqueous sodium chloride solution which is isotonic with the body fluids.

The following examples will further illustrate the invention without, however, limiting it thereto.

EXAMPLE 1

1:2 Molar salt of 1,2-ethanediamine and nalidixic acid

To 25 ml. of 1,2-ethanediamine (large excess) heated to about 75° C. was added with stirring 8.3 g. (0.036 mole) of nalidixic acid and the resulting mixture was heated on a steam bath for one hour. The reaction mixture was cooled in tap water and the separated solid was collected, washed successively with a small quantity of ethylenediamine and then several times with ether, and dried in vacuo at room temperature (20°–25° C.) over potassium hydroxide to produce 8.7 g. of the 1:2 molar salt of 1,2-ethanediamine and nalidixic acid, also named 1,2-ethanediaminium bis-(1-ethyl-1,4-dihydro-7-methyl-4-oxo-1,8-naphthyridine-3-carboxylate), m.p. 216°–219° C. with decomposition, an off-white powder.

EXAMPLE 2

Solution of 1:1 equimolar salt of 1,2-ethanediamine and nalixidic acid

To a suspension containing 2.50 g. (0.0108 mole) of nalidixic acid and 40 ml. of distilled water was added 0.6 g. (0.01 mole) of 1,2-ethanediamine (98%). The mixture was swirled and diluted to 50 ml. with distilled water, stirred at ambient temperature for three hours and then filtered through a sintered glass funnel. The filtrate was diluted to 50 ml. (about 1 ml. of distilled water was added) to produce Solution 2A. The collected solid was washed with fresh distilled water and air dried whereupon 0.09 g. of nalidixic acid was recovered. A 2.0 ml. portion of Solution 2A was added to 500 ml. of 0.9% aqueous sodium chloride solution to produce Solution 2B. A 4.0 ml. portion of Solution 1A was added to 500 ml. of 0.9% aqueous sodium chloride solution to produce Solution 1C. The pH values and nalidixic acid equivalent concentrations of the 1:1 salt of 1,2-ethanediamine and nalidixic acid in the above three solutions are given as follows:

| Solution | pH  | Concentration    |
|----------|-----|------------------|
| 2A       | 9.0 | 48.2 mg./ml.     |
| 2B       | 8.3 | 96.4 mg./500 ml. |
| 2C       | 8.4 | 192.8 mg./500 ml.|

EXAMPLE 3

Solutions of 1:1 equimolar salt of 1,2-ethanediamine and nalidixic acid

To a suspension containing 4.64 g. (0.02 mole) of nalidixic acid and 40 ml. of distilled water was added 1.2 g. (0.02 mole) of 1,2-ethanediamine (98%). Another 0.12 g. (0.002 mole) of 1,2-ethanediamine was added and the resulting mixture was warmed to about 35° C and stirred. A small amount of finely suspended material was filtered off through diatomaceous earth to produce a slightly yellow filtrate containing in theory a nalidixic acid equivalent of 92.8 mg./ml. as its 1:1 equimolar salt of 1,2-ethanediamine; this solution is designated as Solution 3A. A 1.0 ml. portion of Solution 3A was added to 250 ml. of 0.9% sodium chloride solution to produce Solution 3B containing 185.6 mg. of said 1:1 equimolar salt per 500 ml. of solution. Solution 3B was diluted with 500 ml. of 0.9% sodium chloride solution to produce Solution 3C containing 92.8 mg. of said 1:1 equimolar salt per 500 ml. of solution. The respective pH values of Solutions 3A, 3B and 3C are 9.5, 8.9 and 8.7, respectively.

EXAMPLE 4

Solutions of 1:1 equimolar salt of 1,2-ethanediamine and nalidixic acid

To a suspension containing 2.32 g. (0.01 mole) of nalidixic acid suspended in 40 ml. of distilled water was added 0.6 g. (0.01 mole) of 1,2-ethanediamine (98%) and the resulting mixture was stirred at ambient temperature for sixteen hours, diluted to 50 ml. by addition of distilled water and stirred for an additional fifteen minutes. The small quantity of remaining solid was collected on a filter, washed with 2 to 3 ml. of cold water and dried whereupon 0.07 g. of nalidixic acid was recovered. The filtrate, designated Solution 4A, contained 45.0 mg./kg. and had a pH of 9.0. A 2.0 ml. portion and a 4.0 ml. portion of Solution 4A were added each to 500 ml. of 0.9% sodium chloride solution to produce, respectively, Solutions 4B and 4C containing respectively 92.8 mg. and 185.6 mg. of said 1:1 equimolar salt of 1,2-ethanediamine and nalidixic acid per 500 ml. of solution and having respective pH values of 8.3 and 8.4.

EXAMPLE 5

Solution of 1:1 equimolar salt of 1,2-ethanediamine and nalidixic acid

To a suspension containing 2.50 g. (0.0108 mole) of nalidixic acid in 40 ml. of distilled water was added 0.6 g. (0.01 mole) of 1,2-ethanediamine (98%). The mixture was swirled, diluted to 50 ml. by addition of distilled water and stirred at ambient temperature for four hours. A small quantity of remaining solid was filtered off on a sinter glass funnel to produce 50 ml. of filtrate, Solution 5A. The separated solid was washed with water and air dried whereupon 0.17 g. of nalidixic acid was recovered. The corrected weight of nalidixic acid thus is 2.50 minus 0.17 g./50 ml. of solution or an equivalent of 46.6 mg. of nalidixic acid per ml. of solution. The pH of this solution was found to be 9.0.

Alternatively the solution prepared by the procedure described in the immediately preceding paragraph also can be prepared from the 1:2 molar salt of 1,2-ethanediamine and nalidixic acid by the following procedure: to a suspension containing 2.83 g. (0.0054 mole; 0.0108 equivalent of nalidixic acid) of the 1:2 salt of 1,2-ethanediamine and nalidixic acid in 40 ml. of distilled water was added 0.28 g. (0.0046 mole) of 1,2-ethanediamine (98%). The mixture was swirled, diluted to 50 ml. by addition of distilled water and the resulting mixture stirred at ambient temperature for four hours. The small quantity of remaining solid was filtered off on a sinter glass funnel to produce 50 ml. of filtrate to produce Solution 5B. The separated solid was washed with water and air dried to yield 0.12 g. of nalidixic acid formed by disassociation of the 1:2 molar salt of 1,2-ethanediamine and nalidixic acid. Solution 5B thus contains an equivalent of 2.50 minus 0.12 g. or 2.38 g. of nalidixic acid per 50 ml. of solution or 47.6 mg. of nalidixic acid per ml. of solution. This Solution 5B has a pH of 9.0.

Antibacterial Activity

The 1:1 equimolar salt of nalidixic acid and 1,2-ethanediamine was as active antibacterially as the corresponding parent nalidixic acid when tested in both standard in vitro antibacterial tests and against in vivo bacterial infections in mice, as illustrated in the following paragraphs.

Nalidixic acid, the parent acid, and its 1,2-ethanediamine (1:1) salt were tested in vitro against ten screening organisms and they were also tested against the standard *E. coli* (Vogel) systemic infection in mice, the latter in vivo study being carried out using three different routes of administration: oral, subcutaneous and intravenous. The materials and methods used in the comparative antibacterial tests are given in the following paragraphs.

Preparation of Compounds

The parent nalidixic acid was solublized by adding 1.0 ml. of 1 N NaOH to the crystalline acid and water was added to a concentration of 1000 mcg./ml. for the in vitro study or saline to a concentration of 2.5 or 5.0 mg./ml. for the in vivo study. A stock solution of nalidixic acid 1,2-ethanediamine (1:1) salt was prepared from the 1:2 salt according to Example 5 above (refer to Solution 5B); in saline this solution has a concentration equivalent of the nalidixic acid of 47.6 mg./ml. for in vivo studies. A concentration equivalent of the acid of 1000 mcg./ml. for the in vitro studies was obtained by dilution of the stock solution.

Cultures Used for the In Vitro Study Were as Follows:
*Staphylococcus aureus* (Smith)
*Escherichia coli* (Vogel)
*Klebsiella pneumoniae* 39645
*Proteus mirabilis* MGH-1
*Proteus vulgaris* 9920
*Pseudomonas aeruginosa* MGH-2
*Streptococcus pyogenes* C203
*Candida albicans* 10231
*Aspergillus niger* 16404
*Trichophyton mentagrophytes* 9129

Preparation of Cultures

The bacterial cultures for in vitro use were grown in tryptose-phosphate broth with the exception of *Streptococcus pyogenes* which was grown in Brain Heart Infusion broth with 10% normal horse serum added. The cultures were incubated at 37° C. for twenty-four hours. *Candida albicans* was grown in Maltose Peptone No. 3 broth for three days at 25° C. After incubation, these cultures were adjusted to an optical density of 0.10 (640 nm) with water and subsequently diluted in appropriate culture medium to $2 \times 10^5$ cells/ml. The fungi, which are stored at 4° C. as spore suspensions, were diluted in Maltose Peptone No. 3 broth to $2 \times 10^5$ cells/ml.

Tube Dilution Tests

The compounds were tested for antimicrobial activity by a single-row tube dilution method. Serial two-fold dilutions of the 1000 mcg./ml. drug solutions were made in the appropriate culture medium in 0.5 ml. volumes. The tubes were inoculated with 0.5 ml. of the appropriate diluted culture to give a final cell concentration of $10^5$ cells/ml. Minimal inhibitory concentrations (lowest drug concentrations showing no visible growth, designated MIC) were read after eighteen-twenty hours incubation at 37° C. The molds were read after five days incubation at 25° C.

Culture for In Vivo Study *Escherichia coii* (Vogel)

Mice White, Swiss Webster, female, 1820 grams.

Preparation of Inoculum

The *E. coli* culture was grown in Brain Heart Infusion broth at 37° C. for sixteen hours after which 0.1 ml. was removed and inoculated into 10 ml. of Brain Heart Infusion broth and incubated for five hours. This broth culture was diluted 1:32 in saline which resulted in a population of $2 \times 10^7$ cells/ml. All mice to be infected were inoculated intraperitoneally with 0.5 ml. of the inoculum.

Administration of Drug

After inoculation of the organism, the mice were divided into groups of ten. Medication was given to one group of mice at each dose level of each of the four drugs by each of the three routes of administration. Two groups (twenty mice) were used as infection controls. The drugs were administered thirty minutes after the mice were infected. The dose of drug for i.v. injection was contained in 0.2 ml. Those for oral or subcutaneous administration were contained in 0.5 ml. The mice were examined and deaths were recorded for seven days after inoculation. The ED$_{50}$'s (the dose protecting 50% of the mice) were calculated using a modified Reed and Muench method.

Results of In Vitro and In Vivo Tests

The in vitro minimal inhibitory concentrations (MIC's) of the 1-ethanediamine (1:1) salt of nalidixic acid are identical to the MIC's of nalidixic acid against nine of the ten microorganisms examined, as seen in Table I:

Table I

Comparative In Vitro Antibacterial Activity Of Nalidixic Acid and Its 1,2-Ethanediamine (1:1) Salt

| | Minimal Inhibitory Concentration (mcg./ml.) | |
|---|---|---|
| Microorganism | nalidixic acid | 1,2-ED Salt[a] |
| *Staphylococcus aureus* Smith | 31.3 | 31.3 |
| *Escherichia coli* Vogel | 3.9 | 3.9 |
| *Klebsiella pneumoniae* 39645 | 31.3 | 31.3 |
| *Proteus mirabilis* MGH-1 | 15.6 | 15.6 |
| *Proteus vulgaris* 9920 | 1.0 | 1.0 |
| *Pseudomonas aeruginosa* MGH-2 | 125 | 62.5 |
| *Streptococcus pyogenes* C203 | 250 | 250 |
| *Candida albicans* 10231 | 500 | 500 |
| *Aspergillus niger* 16404 | 500 | 500 |

Table I-continued

Comparative In Vitro Antibacterial Activity Of Nalidixic Acid and Its 1,2-Ethanediamine (1:1) Salt

| | Minimal Inhibitory Concentration (mcg./ml.) | |
|---|---|---|
| Microorganism | nalidixic acid | 1,2-ED Salt[a] |
| *Trichophyton mentagrophytes* 9129 | 500 | 500 |

[a]1,2-ED Salt = 1,2-ethanediamine (1:1) salt of nalidixic acid.

In the mouse protection test, no significant differences in ED$_{50}$'s were found between nalidixic acid and its 1,2-ethanediamine salt, as seen in Table II:

Table II

Comparative Efficacy of Nalidixic Acid and Its 1,2-Ethanediamine Salt in a Systemic *Escherichia coli* Infection in Mice

| | ED$_{50}$ (in mg./kg./dose) - Route of Administration | | |
|---|---|---|---|
| Drug | Oral | Intravenous | Subcutaneous |
| Nalidixic acid | 16.5 | 17.6 | 14.0 |
| 1,2-ED Salt[a] | 18.9 | 17.6 | 17.6 |

[a]1,2-ED Salt = 1,2-ethanediamine (1:1) salt of nalidixic acid.

Preferred preparations according to the invention are aqueous solutions of said 1:1 equimolar salt of 1,2-ethanediamine and nalidixic acid for parenteral administration. These solutions may also contain adjuvants such as stabilizing or preserving agents.

I claim:
1. A salt of 1,2-ethanediamine and nalidixic acid.
2. The 1:2 molar salt of 1,2-ethanediamine and nalidixic acid.
3. The 1:1 equimolar salt of 1,2-ethanediamine and nalidixic acid.

* * * * *